(12) United States Patent
Khairkhahan et al.

(10) Patent No.: US 9,242,102 B2
(45) Date of Patent: Jan. 26, 2016

(54) LEADLESS PACEMAKER WITH RADIAL FIXATION MECHANISM

(75) Inventors: Alexander Khairkhahan, Palo Alto, CA (US); Alan Ostroff, Pleasanton, CA (US); Eric Varady, San Francisco, CA (US); Paul Paspa, Los Gatos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 11 days.

(21) Appl. No.: 13/331,922

(22) Filed: Dec. 20, 2011

(65) Prior Publication Data

US 2012/0158111 A1  Jun. 21, 2012

Related U.S. Application Data

(60) Provisional application No. 61/425,064, filed on Dec. 20, 2010.

(51) Int. Cl.
  *A61N 1/372* (2006.01)
  *A61N 1/375* (2006.01)
  *A61N 1/05* (2006.01)

(52) U.S. Cl.
  CPC ............ *A61N 1/37205* (2013.01); *A61N 1/375* (2013.01); *A61N 1/057* (2013.01); *A61N 1/0573* (2013.01); *A61N 1/3756* (2013.01)

(58) Field of Classification Search
  CPC . A61N 1/375; A61N 1/3756; A61N 1/37205; A61N 1/057; A61N 1/0573
  USPC ......... 607/115, 116, 119, 122, 126, 127, 128, 607/131
  See application file for complete search history.

(56) References Cited

U.S. PATENT DOCUMENTS

| 3,199,508 A | 8/1965 | Roth |
| 3,212,496 A | 10/1965 | Preston |

(Continued)

FOREIGN PATENT DOCUMENTS

| DE | 33 00 050 A1 | 7/1984 |
| DE | 33 00050 A1 | 7/1984 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. No. 7,630,767).

(Continued)

*Primary Examiner* — William Levicky
(74) *Attorney, Agent, or Firm* — Theresa A. Raymer (57) ABSTRACT

A leadless cardiac pacemaker having a radial fixation mechanism is provided. The cardiac pacemaker can include fixation mechanism separate from a pacing electrode and having a diameter equal to or less than the outer diameter of the pacemaker. The fixation mechanism can allow the pacemaker to be inserted into tissue with less than 2 rotations of the pacemaker to place the pacing electrode in contact with the tissue. In some embodiments, the fixation mechanism can comprise a plurality of hooks or protrusions positioned near a distal portion of the pacemaker. The fixation mechanism(s) can be configured to penetrate the endocardium of the patient and reside mostly within the myocardium. Methods of delivering the leadless cardiac pacemaker into the heart are also provided.

26 Claims, 6 Drawing Sheets

(56) References Cited

U.S. PATENT DOCUMENTS

| | | |
|---|---|---|
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,649,938 A | 3/1987 | McArthur |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,706,682 A * | 11/1987 | Stypulkowski et al. ...... 600/379 |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |

(56) References Cited

U.S. PATENT DOCUMENTS

| | | |
|---|---|---|
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B1 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |

(56) References Cited

U.S. PATENT DOCUMENTS

| | | |
|---|---|---|
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2* | 4/2006 | Casavant et al. ............. 607/126 |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,599,747 B2* | 10/2009 | Feldmann et al. ............ 607/127 |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |

(56) References Cited

U.S. PATENT DOCUMENTS

| | | | |
|---|---|---|---|
| 2002/0147488 A1 | 10/2002 | Doan et al. | |
| 2003/0141995 A1 | 7/2003 | Lin | |
| 2003/0158584 A1 | 8/2003 | Cates et al. | |
| 2003/0163184 A1 | 8/2003 | Scheiner et al. | |
| 2003/0199941 A1 | 10/2003 | Nielsen et al. | |
| 2003/0204233 A1* | 10/2003 | Laske et al. | 607/127 |
| 2004/0011366 A1 | 1/2004 | Schulman et al. | |
| 2004/0059392 A1 | 3/2004 | Parramon et al. | |
| 2004/0116939 A1 | 6/2004 | Goode | |
| 2004/0133242 A1 | 7/2004 | Chapman et al. | |
| 2004/0143262 A1 | 7/2004 | Visram et al. | |
| 2004/0147973 A1 | 7/2004 | Hauser | |
| 2004/0167587 A1 | 8/2004 | Thompson | |
| 2004/0172116 A1 | 9/2004 | Seifert et al. | |
| 2004/0193223 A1 | 9/2004 | Kramer et al. | |
| 2004/0249417 A1 | 12/2004 | Ransbury et al. | |
| 2004/0260349 A1 | 12/2004 | Stroebel | |
| 2005/0038474 A1 | 2/2005 | Wool | |
| 2005/0038491 A1 | 2/2005 | Haack | |
| 2005/0043765 A1 | 2/2005 | Williams et al. | |
| 2005/0075682 A1 | 4/2005 | Schulman et al. | |
| 2005/0096702 A1 | 5/2005 | Denker et al. | |
| 2005/0131478 A1 | 6/2005 | Kim et al. | |
| 2005/0149138 A1 | 7/2005 | Min et al. | |
| 2005/0165465 A1 | 7/2005 | Pianca et al. | |
| 2005/0267555 A1 | 12/2005 | Marnfeldt et al. | |
| 2005/0288722 A1 | 12/2005 | Eigler et al. | |
| 2006/0064149 A1 | 3/2006 | Belacazar et al. | |
| 2006/0085039 A1 | 4/2006 | Hastings et al. | |
| 2006/0085041 A1* | 4/2006 | Hastings et al. | 607/33 |
| 2006/0085042 A1 | 4/2006 | Hastings et al. | |
| 2006/0105613 A1 | 5/2006 | Carroll | |
| 2006/0108335 A1 | 5/2006 | Zhao et al. | |
| 2006/0121475 A1 | 6/2006 | Davids et al. | |
| 2006/0135999 A1 | 6/2006 | Bodner et al. | |
| 2006/0136004 A1 | 6/2006 | Cowan et al. | |
| 2006/0161222 A1 | 7/2006 | Haubrich et al. | |
| 2006/0241705 A1 | 10/2006 | Neumann et al. | |
| 2006/0247750 A1 | 11/2006 | Seifert et al. | |
| 2006/0282150 A1 | 12/2006 | Olson et al. | |
| 2007/0016263 A1 | 1/2007 | Armstrong et al. | |
| 2007/0043414 A1 | 2/2007 | Fifer et al. | |
| 2007/0055184 A1 | 3/2007 | Echt et al. | |
| 2007/0088394 A1 | 4/2007 | Jacobson | |
| 2007/0088396 A1* | 4/2007 | Jacobson | 607/9 |
| 2007/0088397 A1 | 4/2007 | Jacobson | |
| 2007/0088398 A1 | 4/2007 | Jacobson | |
| 2007/0088418 A1 | 4/2007 | Jacobson | |
| 2007/0123923 A1 | 5/2007 | Lindstrom et al. | |
| 2007/0142709 A1 | 6/2007 | Martone et al. | |
| 2007/0179552 A1 | 8/2007 | Dennis et al. | |
| 2007/0270675 A1 | 11/2007 | Kane et al. | |
| 2007/0276004 A1 | 11/2007 | Hirsch et al. | |
| 2007/0276444 A1 | 11/2007 | Gelbart et al. | |
| 2007/0293904 A1 | 12/2007 | Gelbart et al. | |
| 2008/0004535 A1 | 1/2008 | Smits | |
| 2008/0021532 A1 | 1/2008 | Kveen et al. | |
| 2008/0039738 A1* | 2/2008 | Dinsmoor et al. | 600/547 |
| 2008/0086168 A1 | 4/2008 | Cahill | |
| 2008/0091255 A1 | 4/2008 | Caparso et al. | |
| 2008/0109042 A1* | 5/2008 | Bodner et al. | 607/9 |
| 2008/0119911 A1 | 5/2008 | Rosero | |
| 2008/0243218 A1 | 10/2008 | Bottomley et al. | |
| 2008/0269591 A1 | 10/2008 | Halperin et al. | |
| 2009/0018599 A1 | 1/2009 | Hastings et al. | |
| 2009/0082827 A1 | 3/2009 | Kveen et al. | |
| 2009/0082828 A1* | 3/2009 | Ostroff | 607/36 |
| 2009/0149902 A1 | 6/2009 | Kumar et al. | |
| 2009/0171408 A1 | 7/2009 | Solem | |
| 2009/0204170 A1 | 8/2009 | Hastings et al. | |
| 2010/0069983 A1* | 3/2010 | Peacock et al. | 607/9 |
| 2010/0198288 A1 | 8/2010 | Ostroff | |
| 2010/0211149 A1 | 8/2010 | Morgan et al. | |
| 2010/0249828 A1 | 9/2010 | Mavani et al. | |
| 2010/0274129 A1* | 10/2010 | Hooven | 600/435 |
| 2010/0292541 A1 | 11/2010 | Hashiba et al. | |
| 2010/0305653 A1 | 12/2010 | Lund et al. | |
| 2010/0305656 A1 | 12/2010 | Imran et al. | |
| 2010/0312332 A1 | 12/2010 | Forster et al. | |
| 2011/0004117 A1 | 1/2011 | Neville et al. | |
| 2011/0071586 A1 | 3/2011 | Jacobson | |
| 2011/0077708 A1 | 3/2011 | Ostroff | |
| 2011/0118735 A1* | 5/2011 | Abou-Marie et al. | 606/45 |
| 2011/0208260 A1 | 8/2011 | Jacobson | |
| 2011/0218587 A1 | 9/2011 | Jacobson | |
| 2011/0282423 A1 | 11/2011 | Jacobson | |
| 2012/0245665 A1 | 9/2012 | Friedman et al. | |
| 2013/0041422 A1 | 2/2013 | Jacobson | |
| 2013/0103109 A1 | 4/2013 | Jacobson | |
| 2013/0123875 A1 | 5/2013 | Varady et al. | |
| 2013/0231710 A1 | 9/2013 | Jacobson | |
| 2013/0261597 A1 | 10/2013 | Pertijs et al. | |

FOREIGN PATENT DOCUMENTS

| | | |
|---|---|---|
| EP | 1741465 A1 | 1/2007 |
| JP | H04-506167 A | 10/1992 |
| JP | 05-245215 | 9/1993 |
| JP | 06/507096 | 3/2006 |
| JP | 06/516449 | 7/2006 |
| JP | 2006-526483 A | 11/2006 |
| WO | WO 93/12714 A1 | 7/1993 |
| WO | WO02/34333 A2 | 5/2002 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |
| WO | 2009/006531 A1 | 1/2009 |
| WO | WO2010/088116 A1 | 8/2010 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger; Safety aspects of cardiac pacemakers in magnetic resonance imaging; Dissertation submitted to the Swiss Federal Institute of Technology Zurich; 137 pages; 2002 (month unavailable).

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: In vitro assessment at 1.5 T; Am Heart J; vol. 151; No. 2; pp. 436-443; Feb. 2006.

Khairkhahan et al.; U.S. Appl. No. 13/272,074 entitled "Delivery catheter systems and methods," filed Oct. 12, 2011.

Khairkhahan et al.; U.S. Appl. No. 13/272,082 entitled "Leadless cardiac pacemaker with anti-unscrewing feature," filed Oct. 12, 2011.

Ostroff, Alan; U.S. Appl. No. 13/272,092 entitled "Temperature sensor for a leadless cardiac pacemaker," filed Oct. 12, 2011.

Khairkhahan et al.; U.S. Appl. No. 13/324,781 entitled "Delivery Catheter Systems and Methods," filed Dec. 13, 2011.

(56) References Cited

OTHER PUBLICATIONS

Jacobson et al.; U.S. Appl. No. 13/277,151 entitled "Leadless cardiac pacemaker with conducted communication," filed Oct. 19, 2011.

Khairkhahan et al.; U.S. Appl. No. 13/324,802 entitled "Pacemaker Retrieval Systems and Methods ," filed Dec. 13, 2011.

Ostroff et al.; U.S. Appl. No. 13/910,896 entitled "Leadless Pacemaker with Multiple Electrodes," filed Jun. 5, 2013.

Ostroff, Alan; U.S. Appl. No. 13/915,560 entitled "MRI Compatible Leadless Cardiac Pacemaker," filed Jun. 11, 2013.

Carroll et al.; U.S. Appl. No. 13/956,946 entitled "Biostimulator Circuit with Flying Cell," filed Aug. 1, 2013.

Ostroff, Alan; U.S. Appl. No. 13/967,180 entitled "Leadless Cardiac Pacemaker with Secondary Fixation Capability" filed Aug. 14, 2013.

Ostroff et al; U.S. Appl. No. 13/972,828 entitled "X-Ray Identification for Active Implantable Medical Device" filed Aug. 21, 2013.

International Searching Authority, "Notification of Transmittal of the International Search Report and the Written Opinion of the International Searching Authority, or the Declaration," International Application No. PCT/US2011/066168, Apr. 16, 2012, 9 pages.

International Searching Authority, "International Search Report," International Application No. PCT/US2011/066168, Apr. 16, 2012, 2 pages.

State Intellectual Property Office of the People's Republic of China. "The Second Office Action," Chinese Application No. 201180061312.8, Feb. 27, 2015, 13 pages.

* cited by examiner

LEADLESS PACEMAKER WITH RADIAL FIXATION MECHANISM

CROSS REFERENCE TO RELATED APPLICATIONS

This application claims the benefit of U.S. Provisional Patent Application No. 61/425,064, filed Dec. 20, 2010, titled "LEADLESS PACEMAKER WITH RADIAL FIXATION MECHANISM", which application is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers, and more particularly, to features and methods by which they are attached to heart tissue. More specifically, the present disclosure relates to features and methods for attaching a leadless cardiac pacemaker to tissue with a radial fixation mechanism.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium.

SUMMARY OF THE DISCLOSURE

A leadless cardiac pacemaker is provided, comprising a hermetic housing, a pacing electrode disposed on a distal portion of the housing, an electronics package disposed in the housing, the electronics package configured to generate and deliver pacing signals to the pacing electrode, and a fixation mechanism separate from the pacing electrode and disposed on the distal portion of the housing, the fixation mechanism having a diameter less than or equal to an outer diameter of the hermetic housing and comprising less than two turns of rotation from a distal end of the fixation mechanism to a proximal end of the fixation mechanism.

In some embodiments, the fixation mechanism comprises less than one and a half turns of rotation from the distal end of the fixation mechanism to the proximal end of the fixation mechanism. In other embodiments, the fixation mechanism comprises less than one and a quarter turns of rotation from the distal end of the fixation mechanism to the proximal end of the fixation mechanism.

In some embodiments, the pacing electrode comprises a dome shape. In additional embodiments, the pacing electrode is attached to the housing via a compliant spring to reduce compression force against the heart tissue. In another embodiment, the pacing electrode is attached to the housing via a silicon adhesive to reduce compression force against the heart tissue.

In one embodiment, the fixation mechanism comprises a helix. In some embodiments, the helix rotates less than or equal to 450 degrees. In other embodiments, the helix at least partially surrounds the pacing electrode.

In some embodiments, the fixation mechanism comprises a constant diameter. In another embodiment, the fixation mechanism has a diameter between 2.5 mm and 5 mm.

In some embodiments, the fixation mechanism comprises a longitudinal length of less than 1.8 mm. In other embodiments, the distal portion of the housing has an outer diameter less than an outer diameter of the hermetic housing. In some embodiments, the fixation mechanism is sized and configured so that it does not perforate a myocardium of a patient when fully screwed into cardiac tissue.

In some embodiments, the fixation mechanism comprises a radial portion substantially aligned with a circumference of the housing and a connecting portion attaching the fixation mechanism to the housing. In one embodiment, the radial portion is substantially perpendicular to the connecting portion. In another embodiment, the connecting portion has a length smaller than a thickness of a myocardium layer of a heart of a patient. In yet another embodiment, the connecting portion has a length less than or equal to 1.8 mm. In additional embodiments, the radial portion of the fixation mechanism is configured to reside within a myocardium layer of a heart of a patient and substantially in contact with an endocardium layer of the heart of the patient. In various embodiments, the fixation mechanisms can further comprise a barb disposed on an interior surface of the radial portion of the fixation mechanism.

In another embodiment, the pacemaker is further configured to receive during retrieval a protective sheath having an inner diameter similar to the outer diameter of the hermetic housing.

A method of affixing a pacemaker to tissue in the heart is also provided, comprising positioning a fixation mechanism of the pacemaker adjacent to an endocardium of the heart, the fixation mechanism having a diameter less than or equal to an outer diameter of the pacemaker, piercing the endocardium with the fixation mechanism, and rotating the fixation mechanism less than one and a quarter turns to insert substantially all of the fixation mechanism into the myocardium of the heart and place a pacing electrode of the pacemaker into contact with heart tissue.

In some embodiments, the fixation mechanism comprises a helix. In some embodiments, the pacemaker comprises a leadless cardiac pacemaker.

In another embodiment, the method further comprises covering the pacemaker and fixation mechanism with a protective sheath and removing the pacemaker from the patient.

DETAILED DESCRIPTION OF THE INVENTION

Various embodiments of a leadless cardiac pacemaker having at least one radial fixation mechanism are provided. A leadless cardiac pacemaker can communicate by conducted communication, representing a substantial departure from conventional pacing systems. For example, an illustrative cardiac pacing system can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some pacemakers may further include a secondary fixation mechanism to provide another feature for keeping the biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the biostimulator from moving around in the body in the case of accidental detachment). Further details on secondary fixation mechanisms can be found in U.S. application Ser. No. 12/698,969.

Self-contained or leadless pacemakers or other biostimulators are typically fixed to an intracardial implant site by an actively engaging mechanism such as a screw or helical member that screws into the myocardium. In case of malfunction, it is highly desirable to be able to retrieve the leadless pacemaker of biostimulators both acutely (during the implantation procedure) or chronically, after a period of time post implantation minimally invasively.

Figure 1A:
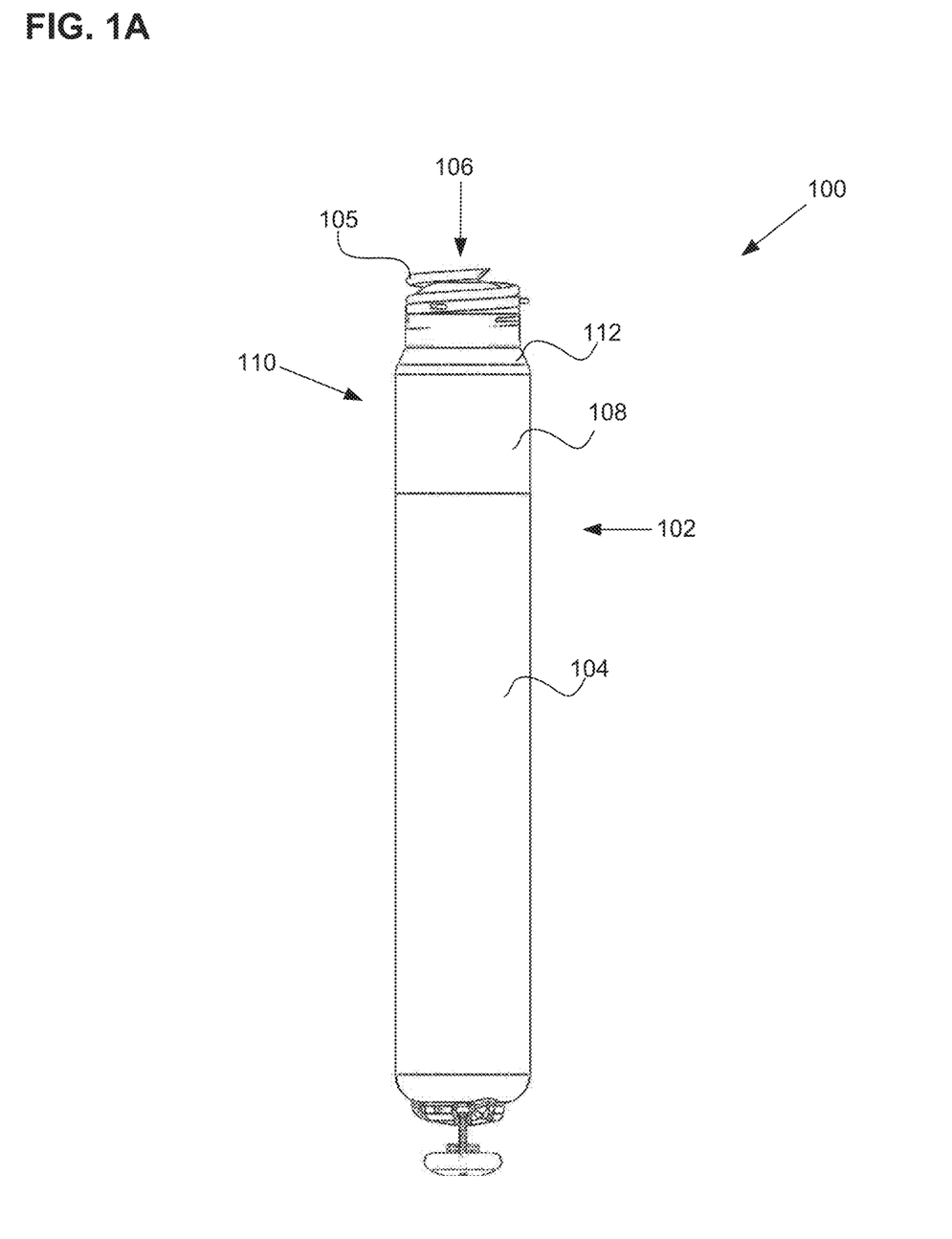
FIGS. 1A-1C illustrate a leadless cardiac pacemaker.

FIG. 1A shows a leadless cardiac pacemaker 100. The biostimulators can include a hermetic housing 102 with electrodes 104 and 106 disposed thereon. As shown, electrode 106 can be separated from but surrounded partially by a fixation mechanism 105, and the electrode 104 can be disposed on the housing 102. The fixation mechanism 105 can be a fixation helix, a plurality of hooks, barbs, or other attaching features configured to attach the pacemaker to tissue, such as heart tissue.

The housing can also include an electronics compartment 110 within the housing that contains the electronic components necessary for operation of the pacemaker, including, for example, a pulse generator, communication electronics, a battery, and a processor for operation. The hermetic housing 102 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In the embodiment of FIG. 1A, a single insulator 108 is disposed along the portion of the housing between electrodes 104 and 106. In some embodiments, the housing itself can comprise an insulator instead of a conductor, such as an alumina ceramic or other similar materials, and the electrodes can be disposed upon the housing.

As shown in FIG. 1A, the pacemaker can further include a header assembly 112 to isolate electrode 104 from electrode 106. The header assembly 112 can be made from PEEK, tecothane or another biocompatible plastic, and can contain a ceramic to metal feedthrough, a glass to metal feedthrough, or other appropriate feedthrough insulator as known in the art.

The electrodes 104 and 106 can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 1A, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A helical fixation mechanism 105, can enable insertion of the device endocardially or epicardially through a guiding catheter. A torqueable catheter can be used to rotate the housing and force the fixation device into heart tissue, thus affixing the fixation device (and also the electrode 106 in FIG. 1A) into contact with stimulable tissue. Electrode 104 can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 1B:
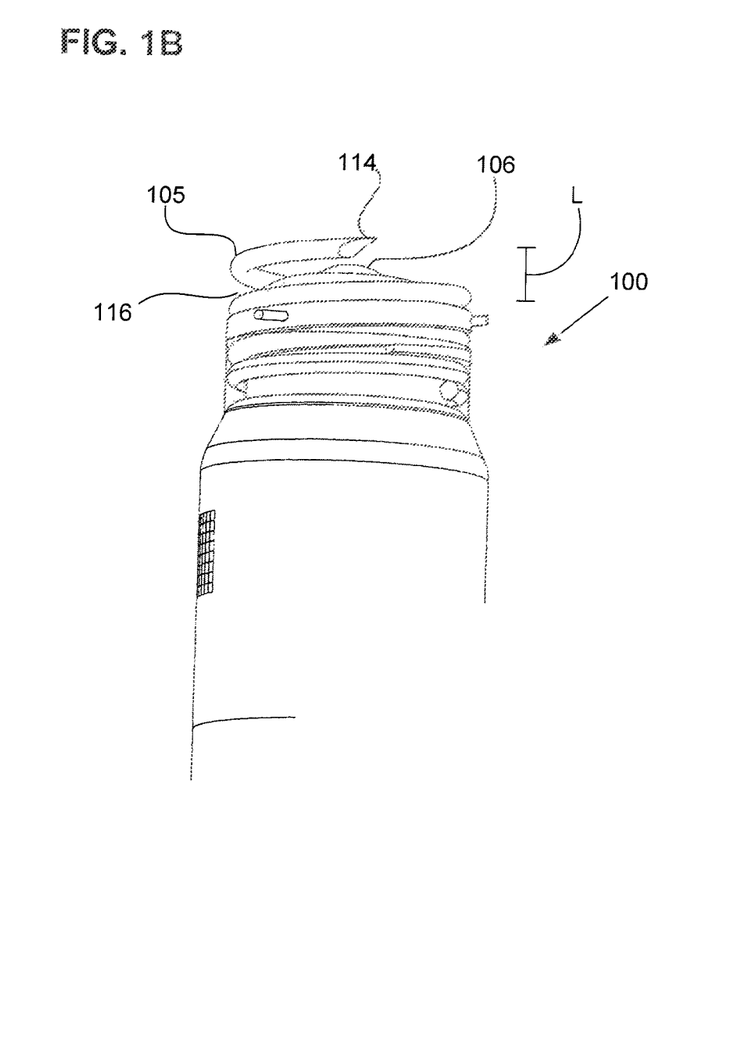
Figure 1C:
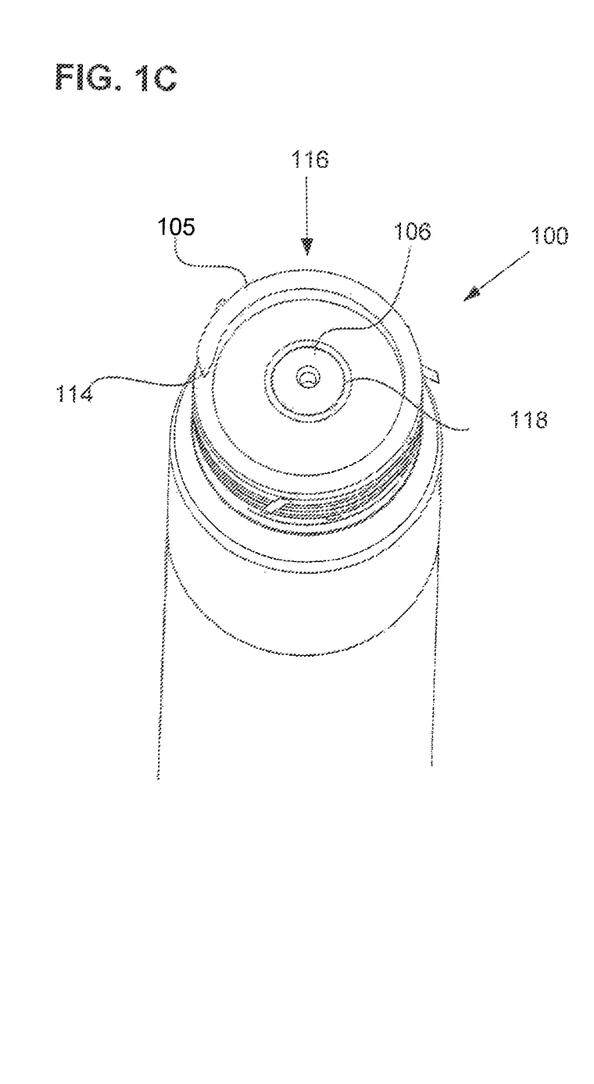

FIGS. 1B-1C illustrate additional close-up views of the distal portion of pacemaker 100, including fixation mechanism 105 and electrode 106. As shown in FIGS. 1B-1C, the fixation mechanism can comprise a helix that partially surrounds or rotates around the electrode 106. In some embodiments, the fixation device comprises a diameter equal to or less than the outer diameter of the housing of the pacemaker itself. In the helical embodiment, the helix can comprise a constant diameter that is less than or equal to the outer diameter of the pacemaker housing. In one embodiment, the fixation device comprises a diameter of less than 5 mm. In another embodiment, the fixation device comprises a diameter of greater than 2.5 mm and less than 5 mm. In some embodiments, the helical fixation device can have a wire diameter of 0.005"-0.03" and a pitch of 0.5 mm to 1.5 mm. Utilizing a fixation mechanism having a diameter up to the diameter of the housing can increase the pull force required to remove the fixation mechanism from tissue, thereby decreasing the chances of the device coming dislodged from the heart. Furthermore, the increased diameter of the fixation mechanism can increase the surface area in contact with the endocardium layer of the heart, further improving the ability of the pacemaker to remain implanted in the patient.

The helical fixation mechanism 105 of FIGS. 1A-1C can comprise a coil having less than 2 full rotations from the leading distal edge of the mechanism to the proximal portion of the mechanism that attaches to the housing of the pacemaker. For example, in FIG. 1B, the distal leading edge 114 of the fixation mechanism 105 is approximately one and a quarter turns (approximately 450 degrees) from proximal end 116 of the fixation mechanism. As shown in FIG. 1B, a distal portion of the housing that attaches to the fixation mechanism can have an outer diameter less than the main outer diameter of the housing, so as to facilitate attachment of the fixation mechanism while allowing the fixation mechanism to have a diameter less than the main outer diameter of the housing.

The fixation mechanism 105 can also include a longitudinal length L of less than 1.8 mm, which is considered the safe length for preventing perforation of the myocardium during implantation. Thus, the fixation mechanism is thereby configured to fully screw into cardiac tissue with less than 2 turns (and preferably less than or equal to one and a quarter turns) without perforating the myocardium of the patient. When the fixation mechanism is fully screwed into the cardiac tissue, the electrode 106 of the pacemaker is in solid contact with the tissue. FIG. 1C shows a top down view of the starting and end points of distal leading edge 114 and proximal end 116 of the fixation mechanism, spanning approximately one and a quarter turns or less. In some other embodiments, the fixation mechanism can span less than 2 full turns from the distal end to the proximal end of the mechanism.

Also shown in FIGS. 1A-1C, the fixation mechanism can include anti-rotation features such as barbs or sutures to prevent counter rotation of the device once it has been screwed into tissue.

Referring to the top down view shown in FIG. 1C, the electrode 106 can comprise a "button" or dome shape that protrudes slightly distally from the distal tip of the pacemaker. The dome shaped electrode can include a diameter of 1.5-2.5 mm and can protrude distally from the end of the pacemaker approximately 0.05" to 0.3". The electrode 106 is preferably an atraumatic surface, and can protrude from the tip of the pacemaker so as to contact the tissue when fixation mechanism 105 is screwed into tissue.

The electrode 106 may be electrically and mechanically attached to the pacemaker via a compliant spring 118 and/or silicone adhesive (not shown), so as to reduce the tensile or compression force and rubbing motion imparted to the tissue to be stimulated. A reduction in force and/or rubbing motion of the electrode relative to tissue to be stimulated will result in a reduction of the tissue's inflammatory response at the electrode/tissue interface, resulting in a reduction of fibrotic tissue formation. This reduction of fibrosis results in a lower pacing voltage/current required to stimulate viable tissue.

In conventional pacemakers, it is common to integrate the pacing electrode into the fixation device itself. However, this combination can cause additional irritation to tissue since the pacing electrode contacts tissue damaged by the fixation device during insertion. By separating the electrode 106 from the fixation device 105, as shown in FIGS. 1B-1C, pacing functions performed by the electrode 106 do not contact tissues otherwise irritated by the fixation device 105. The forces generated by the weight and motion of the pacemaker are intended to be distributed to the tissue in direct contact with the fixation mechanism, and not by the tissue in contact with the electrode 106 located a short distance away. By decoupling the fixation site from the stimulation site, the resulting fibrosis at the distal tip can be reduced, resulting in a reduction of required voltage and current to stimulate viable tissue. Moreover, since the area to be stimulated does not experience irritation due to fixation trauma, the current of injury can be lowered, and low stimulation thresholds can be achieved upon immediate electrode contact.

Figure 2A:
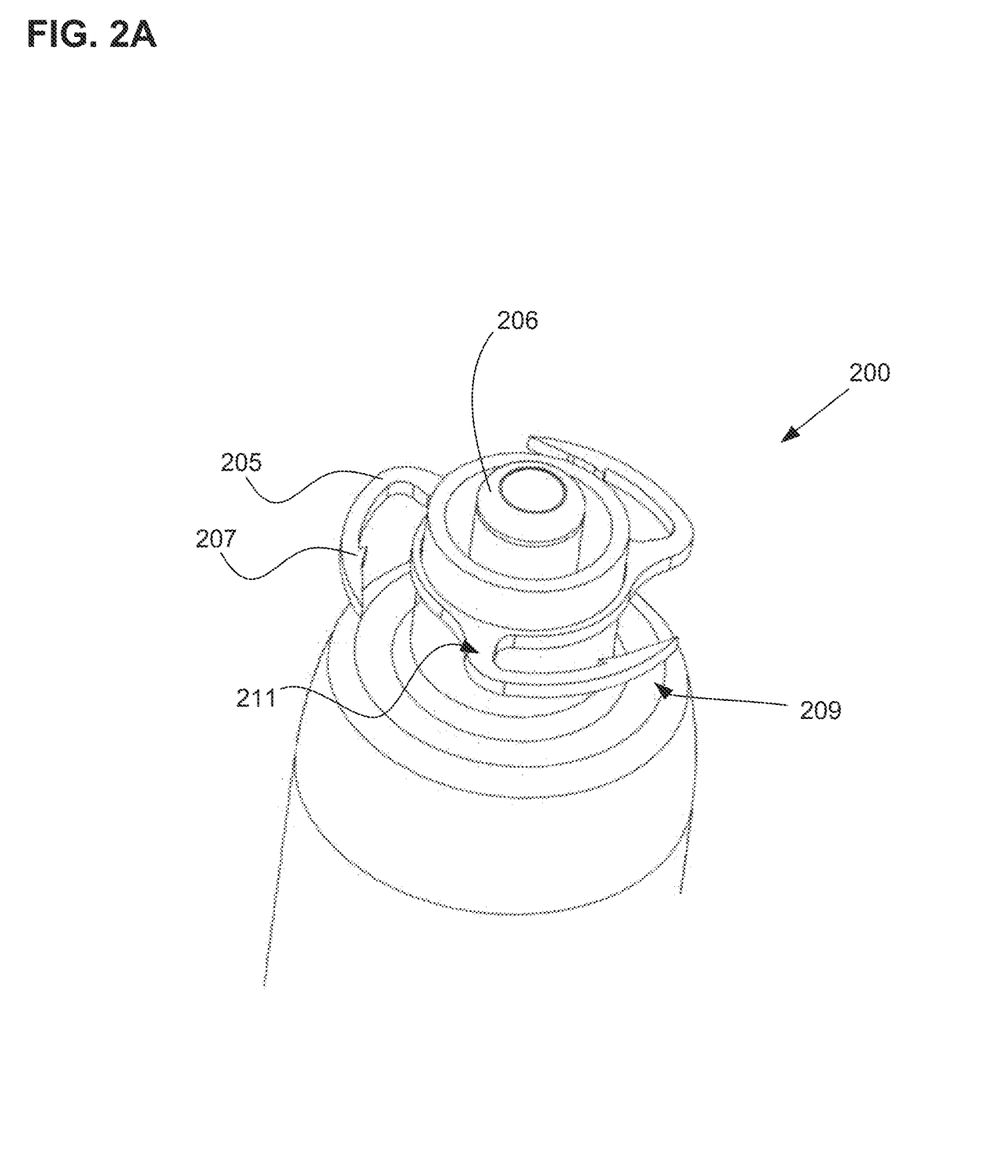
FIGS. 2A-2D are various views of a leadless cardiac pacemaker having a radial fixation mechanism.
Figure 2B:
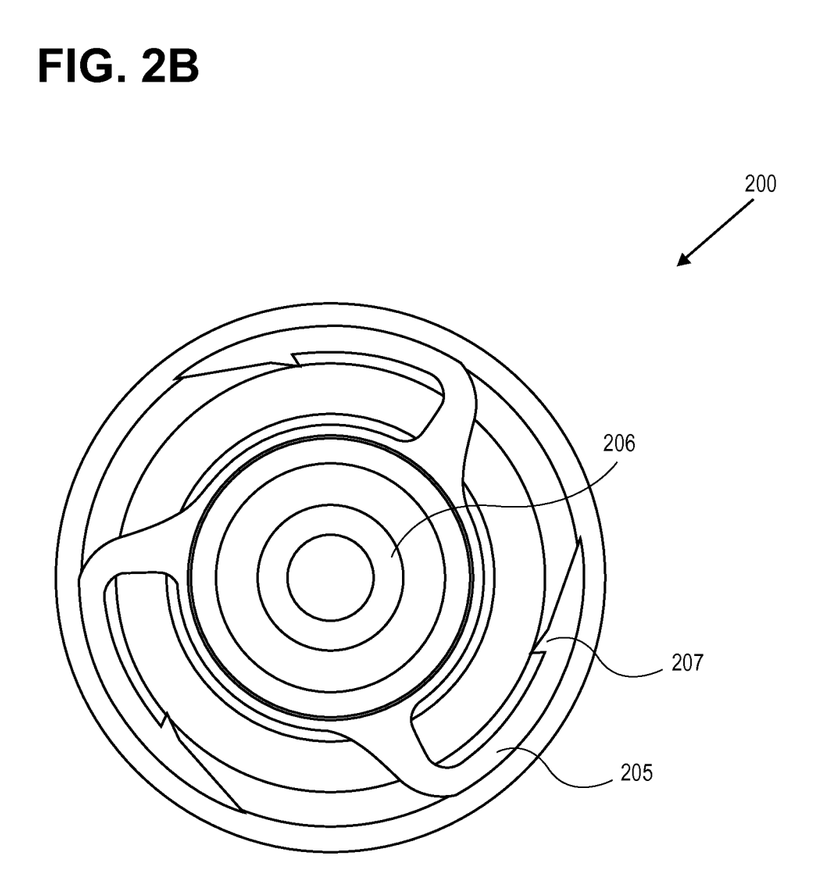
Figure 2C:
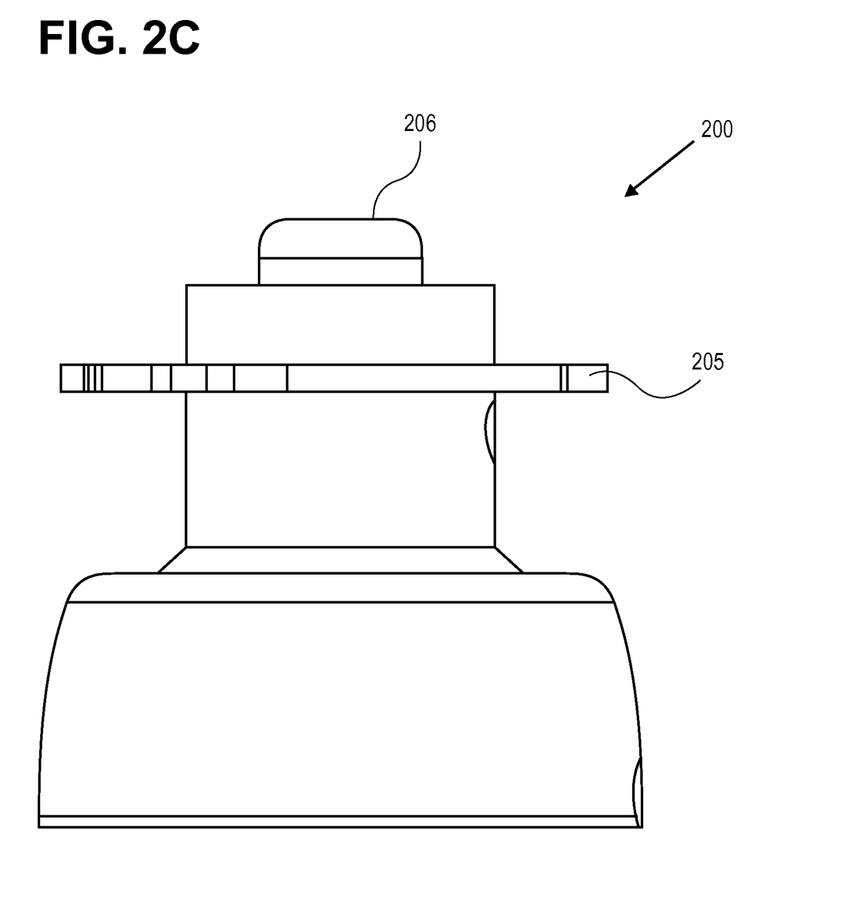

FIGS. 2A-2C illustrate various views of a leadless pacemaker 100 having at least one radial fixation mechanism 205 configured to attach the pacemaker to heart tissue. The radial fixation mechanisms (i.e. hooks, protrusions, spears, etc) can extend radially outwards a distance of less than or equal to the maximum outer diameter (OD) of the housing of the leadless cardiac pacemaker 200, and can be located near the distal portion of the pacemaker. In some embodiments, the radial fixation mechanisms can be relied upon as a secure cardiac fixation mechanism when engaged into cardiac tissue through rotation of the pacemaker.

In the embodiment of FIGS. 2A-2C, the fixation mechanisms comprise multiple L-shaped hooks disposed around or near electrode 206. FIG. 2A shows a perspective view of one embodiment of a pacemaker including three L-shaped hooks or fixation mechanisms. FIG. 2B shows a top down view of the pacemaker of FIG. 2A, and FIG. 2C illustrates a side view of the pacemaker of FIG. 2A, showing the position of the fixation mechanisms with respect to electrode 206. The hooks can comprise a tissue piercing distal tip, as shown, for puncturing heart tissue and particularly for piercing the endocardium of the heart.

The fixation mechanisms 205 of FIGS. 2A-2C are configured to affix to tissue with a shortened radial turn or twist. Referring to FIG. 2A, each fixation mechanism can include a radial portion 209, which runs substantially parallel to a circumference of the pacemaker housing, and a connecting portion 211, which is substantially perpendicular to the radial portion and connects the radial portion to the pacemaker. The connecting portion can be, for example, approximately the same length as the average thickness of the myocardium of the heart. In use, the radial portion of the fixation mechanism is the portion that punctures and affixes to tissue. Turning or screwing the fixation mechanism into tissue will cause the radial portion to engage the tissue until reaching the connecting portion of the fixation mechanism. This can also provide a tactile response by "stopping" rotation of the device when the connecting portion contacts the tissue.

In the embodiment shown in FIGS. 2A-2C, the pacemaker 200 includes three L-shaped radial hooks or barbs. Each hook can comprise, for example, approximately 60-90 degrees or one quarter to one sixth of a turn of the pacemaker to deposit the hook within tissue. The larger the number of hooks used, and therefore the smaller the length of the hook, the fewer the number of turns is required to engage tissue with the hook.

Figure 2D:
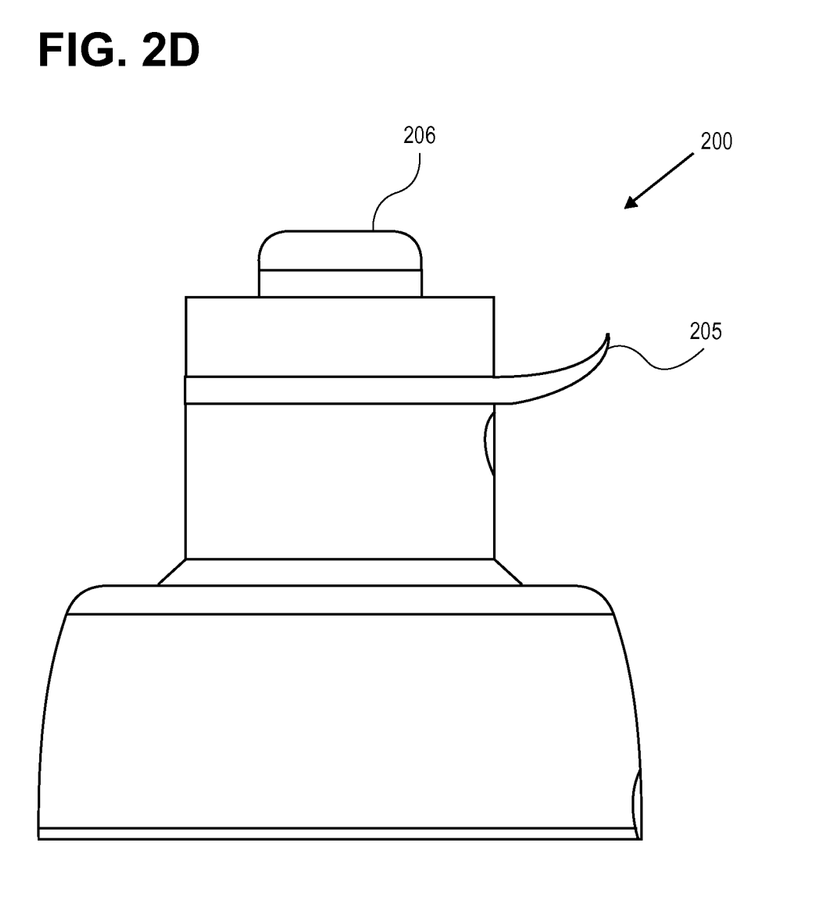

FIG. 2D illustrates another embodiment of a pacemaker 200 having a distally curved radial hook 205. As shown in FIG. 2D, the hook can be curved distally towards the electrode 206 at an angle up to and including 45 degrees from horizontal. Curving the hooks distally towards the electrode can aid in bringing the electrode into contact with the hooks during insertion into tissue. In some embodiments, the angle of curvature can be between 30 and 60 degrees in the distal direction.

The fixation mechanisms can be enclosed in a delivery and retrieval catheter's collapsible sheath (not shown) to allow for easy delivery, repositioning, and retrieval of the leadless pacemaker to and from the right atrium or ventricle. Since the fixation mechanisms always have a diameter less than the outer diameter of the pacemaker, retrieval with a sheath is feasible. In contrast, pacemakers having barbs or hooks larger than the outer diameter of the pacemaker are difficult or unable to be retrieved from the patient due to the inability to cover the larger hooks or barbs with a protective sheath. Examples of a suitable retrieval catheter and sheath can be found in co-pending Application Ser. No. 13/324,802.

These fixation mechanisms can also include features to prevent unscrewing of the pacemaker, such a barbs 207 (a backward-facing point or feature on said fixation mechanism intended to grab tissue and increase the amount of force or torque required to remove the mechanism) and/or holes and indentations that allow for tissue adhesion and in-growth. The fixation mechanisms can be electrically isolated (floating) from the indifferent return electrode of the pacemaker. Because more than one fixation mechanism can be integrated onto the pacemaker, the idea provides redundant fixation means.

The innermost layer of tissue that lines the chamber of the heart is the thin but tough endocardium. Beneath it lays the soft myocardium, the cardiac muscle tissue comprising the majority of the thickness of the heart wall. When the fixation mechanism or mechanisms described above are engaged in acute cardiac tissue, the sharpened tip pierces the endocardium and enters the myocardium until the majority of its length resides in the myocardium. It is the thin but strong endocardium that provides the majority of the fixation mechanism's holding force in tissue. The hook design of the fixation mechanisms as shown in FIGS. 2A-2C can provide superior holding force over alternative designs (e.g. small helices) due to the large contact surface between the endocardium and the underlying the hooks. More specifically, the radial portion 209 of the hooks can be angled and aligned to maximize the contact surface between the hook and endocardium, as shown in FIG. 2D.

Moreover, the small barb features (e.g., barbs 207) implemented on each hook are configured to grab the endocardium from within as the hook slides back out of the puncture site as the pacemaker is unscrewed. Barb features may be designed quite small (on the order of 0.01") to sufficiently grab endocardium upon removal, but would have to be designed unacceptably large to have the same holding force in myocardium alone.

Because the small barbs 207 are designed to hold the endocardium, the number and position of the barbs on each fixation mechanism is another area of design flexibility. Each hook 205 may have one or more barbs positioned distally, proximally, and in-between. In some embodiments, two barbs per fixation mechanism is sufficient—one positioned proximally near the base of each hook, and one positioned distally near each fixation mechanism's sharpened point. When a hook is properly engaged in cardiac tissue, a majority of the hook (e.g., the radial portion of the hook) has punctured the endocardium and is disposed within the myocardium. In this case, the proximal barb would then be positioned directly behind the endocardium; after only a few degrees of angular unscrewing, these proximal barbs would immediately grab the endocardium and prevent further unscrewing. The distal barbs near the ends of the fixation mechanisms are positioned in the case the hooks are not 100% engaged in tissue; as long as a few degrees of engagement have occurred, these distal barbs would be in-tissue and can be relied upon to prevent dislodgement.

The fixation mechanisms with barbs can be created by a number of processes known to those with skill in the art. For example, an axisymmetric multiple fixation mechanism with barbs can be cut from a sheet of metal via a laser, wire EDM, or chemical etching. Metal parts can also be manufactured using metal-injection-molding techniques. Certain edges can be rounded or sharpened through electropolishing or tumbling techniques. Plastic parts may also be cut from a sheet or injection-molded.

Barbs 207 can be formed on any face or combination of faces of each individual hook, though the easiest two faces would be the surface facing inwards toward the pacemaker and the face facing outwards towards the tissue. Placing barbs only on the inward-facing surface has the advantage of achieving the anti-unscrewing design objective while leaving the outward-facing surfaces smooth, reducing the risk of snagging or ripping tissue or the catheter's protective sheath during delivery, repositioning, or retrieval.

The mechanical characteristics of the hooks and barbs can be varied through the selection of the hook material and the cross-sectional profile. They may be designed to be axially stiff by increasing their axial thickness (increasing the thickness of the sheet they are cut from) while designed to be radially flexible by reducing their cut profile strut width. The hooks can manufactured out of plastic or metal. They can be made rigid through the use of glass-filled polymers or hard metals such as MP35N, Stainless Steel, or titanium. They can also be designed to be elastic by manufacturing the hooks out of flexible polymers or superelastic nitinol. Moreover, they can be manufactured partially or entirely out of a bioabsorbable polymer so that they provide secure acute fixation but allow for easier chronic retrieval. The fixation hooks can be made porous or coated with a high-microscopic-surface-area coating to promote chronic tissue in-growth and/or adhesion. The hooks may also be coated with a steroid similar to that used for electrodes to reduce the resulting fibrotic response.

The angle of the hooks may also be adjusted to tailor the fixation performance. When the pacemaker is positioned at the apex of a ventricle and is rotated to engage tissue, the angle of the hooks can determine whether the pacemaker is pulled or pushed in the distal or proximal direction as the hooks follow their trajectory into the cardiac tissue. If the hooks are angled down (such that the sharpened tips of the hooks are more distal than the base of the hooks), then the pacemaker will move in the distal direction as the pacemaker is rotated. This additional distal motion of the pacemaker can ensure that its distal electrode is drawn closer to the distal endocardial stimulable tissue and will remain in contact with that tissue.

This configuration allows for the positioning of a conventional steroid endocardial pacing electrode along the central axis at the distal tip. This electrode can be used as the primary pacing/sensing tip electrode, located a few millimeters away from this disclosed fixation mechanism.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A leadless cardiac pacemaker, comprising:
a hermetic housing;
a pacing electrode disposed on a distal portion of the housing, the electrode comprising an atraumatic surface not configured to penetrate heart tissue;
an electronics package disposed in the housing; and
a fixation mechanism located a distance from the pacing electrode and disposed on the distal portion of the housing, the fixation mechanism comprising a helix having a longitudinal length,
wherein the helix is configured to pierce an endocardium layer of the patient's heart and to rotate into a myocardium layer of the patient's heart, the helix remaining in contact with the endocardium layer of the heart and the pacing electrode being placed into contact with the patient's heart tissue when the helix is fully rotated into the heart tissue, and
wherein the helix comprises a constant diameter and is positioned about the pacing electrode to at least partially surround the pacing electrode so that the electrode does not contact tissue of the patient's heart that is irritated due to fixation trauma.

2. A leadless cardiac pacemaker, comprising:
a hermetic housing;
a pacing electrode disposed on a distal portion of the housing, the electrode comprising an atraumatic surface;
an electronics package disposed in the housing; and
a fixation mechanism separated from the pacing electrode and disposed on the distal portion of the housing, the fixation mechanism comprising a helix having a longitudinal length, wherein the helix is configured to pierce an endocardium layer of the patient's heart and to screw into a myocardium layer of the patient's heart, the helix remaining in contact with the endocardium layer of the heart and the pacing electrode being placed into contact with the patient's heart tissue at a stimulation site when the fixation mechanism is fully screwed into a fixation site, and wherein the helix comprises a constant diameter and is positioned about the pacing electrode to at least partially surround the pacing electrode so that the electrode does not contact tissue of the patient's heart that is irritated due to the fixation mechanism when the fixation mechanism is fully screwed into the fixation site.

3. The leadless cardiac pacemaker of claim 2, wherein the fixation site of the leadless pacemaker is decoupled from the stimulation site so that the stimulation site does not experience irritation due to fixation trauma during implantation of the leadless cardiac pacemaker.

4. The leadless cardiac pacemaker of claim 2, wherein the constant diameter of the fixation mechanism is equal to a diameter of the hermetic housing.

5. The pacemaker of claim 2 wherein the constant diameter of the fixation mechanism is between 2.5 mm and 5 mm, and wherein the fixation mechanism has a pitch of 0.5 mm to 1.5 mm.

6. The pacemaker of claim 2 wherein the longitudinal length of the helix is less than 1.8 mm.

7. The pacemaker of claim 2 wherein the electrode is configured not to penetrate the patient's heart.

8. A leadless cardiac pacemaker, comprising:
a hermetic housing;
a pacing electrode disposed on a distal portion of the housing;
an electronics package disposed in the housing; and
a fixation mechanism separate from the pacing electrode and disposed on the distal portion of the housing, the fixation mechanism comprising a helix having a longitudinal length, wherein the helix is configured to penetrate the endocardium layer of the patient's heart and rotate into a myocardium layer of the patient's heart, the helix configured to remain in contact with the endocardium layer of the heart when the helix is fully screwed into cardiac tissue, wherein the helix comprises a constant diameter and is positioned about the pacing electrode to at least partially surround the pacing electrode so that that the helix secures to the cardiac tissue at a fixation site that is separate and decoupled from a stimulation site contacted by the pacing electrode, wherein the pacing electrode comprises a dome shape having an atraumatic surface.

9. The pacemaker of claim 8 wherein the pacing electrode is attached to the housing via a compliant spring to reduce compression force against the heart tissue.

10. The pacemaker of claim 8 wherein the pacing electrode is attached to the housing via a silicone adhesive to reduce compression force against the heart tissue.

11. The pacemaker of claim 8 wherein the constant diameter of the fixation mechanism is between 2.5 mm and 5 mm.

12. The pacemaker of claim 8 wherein the longitudinal length of the helix is less than 1.8 mm.

13. The pacemaker of claim 8 wherein the constant diameter of the fixation mechanism is less than a diameter of the hermetic housing.

14. The pacemaker of claim 8 wherein the fixation mechanism is sized and configured so that it does not perforate the myocardium layer when fully screwed into the cardiac tissue.

15. The pacemaker of claim 8 wherein the fixation mechanism comprises a barb to resist counter rotation of the fixation mechanism when the fixation mechanism is screwed into the cardiac tissue.

16. The pacemaker of claim 8 being further configured to receive during retrieval a protective sheath having an inner diameter similar to an outer diameter of the hermetic housing.

17. The pacemaker of claim 8, wherein the constant diameter of the fixation mechanism is equal to a diameter of the hermetic housing.

18. The pacemaker of claim 8, wherein the pacing electrode protrudes approximately 0.05 to 0.3 inches from the distal portion of the housing.

19. The pacemaker of claim 8, wherein the pacing electrode is configured not to penetrate the patient's heart.

20. A leadless cardiac pacemaker, comprising:
a hermetic housing;
a pacing electrode disposed on a distal portion of the housing, the pacing electrode comprising a dome shape having an atraumatic surface;
an electronics package disposed in the housing; and
a fixation mechanism separate from the pacing electrode and disposed on the distal portion of the housing, the fixation mechanism comprising a helix configured to penetrate the endocardium layer of the patient's heart and rotate into a myocardium layer of the patient's heart, the helix configured to remain in contact with the endocardium layer of the heart when the helix is fully screwed into cardiac tissue, wherein a smallest diameter of the helix is greater than a diameter of the pacing electrode, and wherein the helix is positioned about the pacing electrode to at least partially surround the pacing electrode so that that the helix secures to the cardiac tissue at a fixation site that is separate and decoupled from a stimulation site contacted by the pacing electrode.

21. The pacemaker of claim 20 wherein the smallest diameter of the helix is greater than twice the diameter of the pacing electrode.

22. The pacemaker of claim 20 wherein the helix comprises a constant diameter.

23. A leadless cardiac pacemaker, comprising:
a hermetic housing;
a pacing electrode disposed on a distal portion of the housing, the electrode comprising an atraumatic surface not configured to penetrate heart tissue;
an electronics package disposed in the housing; and
a fixation mechanism located a distance from the pacing electrode and disposed on the distal portion of the housing, the fixation mechanism comprising a helix,
wherein the helix is configured to pierce an endocardium layer of the patient's heart and to rotate into a myocardium layer of the patient's heart, the helix remaining in contact with the endocardium layer of the heart and the pacing electrode being placed into contact with the patient's heart tissue when the helix is fully rotated into the heart tissue, and
wherein the helix comprises a constant diameter equal to a constant diameter of the distal portion of the housing, and is positioned about the pacing electrode to at least partially surround the pacing electrode so that the electrode does not contact tissue of the patient's heart that is irritated due to fixation trauma.

24. The pacemaker of claim 23 wherein a proximal portion of the housing comprises a constant diameter greater than the constant diameter of the distal portion of the housing.

25. The pacemaker of claim 24 wherein the housing further comprises an intermediate portion coupling the proximal portion to the distal portion, the intermediate portion having a diameter that transitions linearly from the constant diameter of the proximal portion to the constant diameter of the distal portion.

26. A leadless cardiac pacemaker, comprising:
a hermetic housing;
a pacing electrode disposed on a distal portion of the housing, the electrode comprising an atraumatic surface, the distal portion of the housing comprising a flat surface adjoining and surrounding the pacing electrode, and the distal portion of the housing further comprising a rounded edge adjoining and surrounding the flat surface;
an electronics package disposed in the housing; and
a fixation mechanism separated from the pacing electrode and disposed on the distal portion of the housing, the fixation mechanism comprising a helix,
wherein the helix is configured to pierce an endocardium layer of the patient's heart and to screw into a myocardium layer of the patient's heart, the helix remaining in contact with the endocardium layer of the heart and the pacing electrode being placed into contact with the patient's heart tissue at a stimulation site when the fixation mechanism is fully screwed into a fixation site, and
wherein the helix comprises a constant diameter and is positioned about the pacing electrode to at least partially surround the pacing electrode so that the electrode does not contact tissue of the patient's heart that is irritated due to the fixation mechanism when the fixation mechanism is fully screwed into the fixation site.

* * * * *